(12) United States Patent
Lu et al.

(10) Patent No.: US 10,543,471 B2
(45) Date of Patent: Jan. 28, 2020

(54) THERMOSENSITIVE NANOCAPSULES AND PREPARING METHOD THEREOF

(71) Applicant: ANHUI MICRODELIVERY SMART MICROCAPSULE SCI & TECH CO. LTD, Tongling (CN)

(72) Inventors: Xihua Lu, Tongling (CN); Di Zhao, Tongling (CN); Liying Wang, Tongling (CN)

(73) Assignee: ANHUI MICRODELIVERY SMART MICROCAPSULE SCI & TECH CO. LTD, Tongling (CN)

( * ) Notice: Subject to any disclaimer, the term of this patent is extended or adjusted under 35 U.S.C. 154(b) by 0 days.

(21) Appl. No.: 16/313,909

(22) PCT Filed: Jul. 1, 2016

(86) PCT No.: PCT/CN2016/088133
§ 371 (c)(1),
(2) Date: Dec. 28, 2018

(87) PCT Pub. No.: WO2018/000423
PCT Pub. Date: Jan. 4, 2018

(65) Prior Publication Data
US 2019/0329211 A1    Oct. 31, 2019

(30) Foreign Application Priority Data
Jun. 29, 2016    (CN) .......................... 2016 1 0504888

(51) Int. Cl.
*A23L 27/00* (2016.01)
*A61K 8/35* (2006.01)
*C11B 9/00* (2006.01)
*B01J 13/18* (2006.01)
*A61K 8/11* (2006.01)
*A61K 8/37* (2006.01)
*A61K 8/40* (2006.01)
*A61K 9/00* (2006.01)
*A61K 9/51* (2006.01)
*A61Q 13/00* (2006.01)
*A61Q 17/04* (2006.01)
*B01J 13/02* (2006.01)

(52) U.S. Cl.
CPC ............ *B01J 13/185* (2013.01); *A23L 27/72* (2016.08); *A23L 27/74* (2016.08); *A61K 8/11* (2013.01); *A61K 8/35* (2013.01); *A61K 8/37* (2013.01); *A61K 8/40* (2013.01); *A61K 9/0004* (2013.01); *A61K 9/5123* (2013.01); *A61K 9/5138* (2013.01); *A61K 9/5192* (2013.01); *A61Q 13/00* (2013.01); *A61Q 17/04* (2013.01); *B01J 13/025* (2013.01); *C11B 9/0003* (2013.01); *A23V 2002/00* (2013.01)

(58) Field of Classification Search
CPC ........ A61K 47/32; A61K 47/34; A61K 9/107; A61K 9/51; A61K 8/11; A61K 8/35; A61K 8/37; A61K 8/40; A61K 9/0004; A61K 9/5123; A61K 9/5138; A61K 9/5192; A61P 3/02; A61P 35/00; B01J 13/025; B01J 13/16; B01J 13/185; C08F 2/26; C08F 2/30; C08F 2/44; C08F 220/54; C08F 4/04; C08F 4/34; A23L 27/72; A23L 27/74; A61Q 13/00; A61Q 17/04; C11B 9/0003; A23V 2002/00
See application file for complete search history.

(56) References Cited

U.S. PATENT DOCUMENTS

2012/0187346 A1* 7/2012 Chun ..................... C08F 2/22
252/500

FOREIGN PATENT DOCUMENTS

| CN | 102525882 A | 7/2012 |
| CN | 103764172 A | 4/2014 |
| CN | 103965421 A | 8/2014 |

OTHER PUBLICATIONS

Di Zhao et al, Polymerization mechanism of poly( ethylene glycol dimethacrylate) fragrance nanocapsules, Royal Society of Chemistry, Oct. 29, 2015, pp. 96067-96073.
Cong Liu et al, Preparation and characteristics of nanocapsules containing essential oil for textile application, Flavor and Fragrance Journal, 2015, pp. 295-301.
(Continued)

Primary Examiner — Irina S Zemel
(74) Attorney, Agent, or Firm — Gokalp Bayramoglu (57) ABSTRACT

The present invention discloses a thermosensitive nanocapsule and a preparing method thereof. The thermosensitive nanocapsule includes core materials and wall materials. The preparing method includes: first, making water phase and oil phase respectively, forming microemulsion by means of high speed shearing after mixing, and forming nanoemulsion via ultrasonic treatment or high pressure homogenization; then adding nitrogen to the emulsion and carrying out the reaction under a temperature of 40-80° C. for 3-4 hrs in the nitrogen atmosphere; finally obtaining the thermosensitive nanocapsule with an embedding rate of 90-94%, a particle size of less than 150 nm and a dimension polydispersity index of 0.09-0.17. In present invention, the monomer that forms the wall material of the nanocapsules is made from common biological materials, and has a good biocompatibility. The wall material has a temperature sensitivity, and can control the delayed release of core material by adjusting temperature.

16 Claims, 2 Drawing Sheets

(56) References Cited

OTHER PUBLICATIONS

Zhihai Cao et al, Synthesis of fragrance/silica nanocapsules through a sol-gel process in miniemulsions and their application as aromatic finishing agents, Colloid Polym Sci, (2015) 293 pp. 1129-1139.
Baharak Hosseinkhani et al, Novel biocompatible nanocapsules for slow release of fragrances on the human skin, New Biotechnology, vol. 32, No. 1, Jan. 2015, pp. 40-46.

* cited by examiner

THERMOSENSITIVE NANOCAPSULES AND PREPARING METHOD THEREOF

CROSS REFERENCE TO THE RELATED APPLICATIONS

This application is the national phase entry of International Application No. PCT/CN2016/088133, filed on Jul. 1, 2016, which is based upon and claims priority to Chinese Patent Application No. 201610504888.1, filed on Jun. 29, 2016, the entire contents of which are incorporated herein by reference.

TECHNICAL FIELD

The present invention belongs to the field of nanocapsules and their preparation technology, and more particularly, relates to the composition and method for preparing thermosensitive nanocapsules.

BACKGROUND

In general, the dimension of microcapsules typically ranges between 1 and 1000 μm. With the development of microcapsule technology and nanotechnology, the so-called nanocapsules with a size of less than 1 μm, i.e., 1-1000 nm, could also be obtained. Prior to the traditional microcapsules, nanocapsules promise the advantages of: (1) facilitation for further surface modification, increasing embedding rate, and varying distribution or targetability; (2) high stability facilitating processing, storage and transportation; (3) good biocompatibility with little toxicity or side effects; (4) potential for delayed release particles to prolong drug efficacy; (5) exemption from doing harm to other components when used in food. As a matter of fact, nanocapsule technology has been listed as the major R&D high-tech in the 21st century, and nanocapsules have been applied in food condiments, agriculture and biotechnology, biomedicine, cosmetics, textiles and other fields.

Quite a lot works have been reported concerning the preparation of nanocapsules. Zhao et al. (Polymerization Mechanism of Poly(Ethylene Glycol Dimethacrylate) Fragrance Nanocapsules, RSC Advances. 2015, 5(116), 96067-96073) embedded flavor with miniemulsion polymerized nanocapsules without thermosensitivity. Liu et al. (Preparation and characteristics of nanocapsules containing essential oil for textile application, Flavour and Fragrance Journal 2015, 30(4), 295-301) obtained emulsion polymerized flavor nanocapsules just with a embedding rate of 85.4%. Cao et al. (Synthesis of fragrance/silica nanocapsules through a sol-gel process in miniemulsions and their application as aromatic finishing agents, Colloid and Polymer Science 2015, 293(4), 1129-1139) prepared nanocapsules by means of sol-gel method in a reaction system with certain toxicity. Moreover, Hosseinkhani et al. (Novel biocompatible nanocapsules for slow release of fragrances on the human skin, New Biotechnology 2015, 32(1), 40-46) made flavor nanocapsules without thermosensitive release performance with nano-precipitation method. In conclusion, there is no report on the preparation of nanocapsules with good biocompatibility, high embedding rate and controlled release. Nevertheless, the present invention adopts a green, environmentally friendly, simple and mild preparation system to provide nanocapsules with non-toxicity, high embedding rate, temperature sensitivity and controlled slow release performance, which have broad application prospects in the fields of medicine, daily chemicals, textiles, etc.

SUMMARY

A primary object of the present invention is to provide a composition and method for making nanocapsules could be applied in the fields of flavors and fragrances, biomedicine, daily cosmetics and textiles, wherein the nanocapsules have a uniform dimension and a particle size of less 150 nm, and possess non-toxicity, high embedding rate, temperature sensitivity and controlled slow release performance.

Another object of the present invention is to provide a method for preparing thermosensitive nanocapsules, wherein the used two different N-alkyl acrylamide monomers are of good biocompatibility and non-toxicity, hence would not leave the unreacted toxic monomer residues.

Another object of the present invention is to provide a method for preparing thermosensitive nanocapsules, wherein the wall material is of non-toxicity and good thermosensitivity, hence could be well applied in products related to human body.

Another object of the present invention is to provide a method for preparing thermosensitive nanocapsules, wherein the used emulsifier is non-toxic and environmentally friendly, hence would not introduce any toxic substances into the reaction system.

Another object of the present invention is to provide a method for preparing thermosensitive nanocapsules, wherein the used initiator can decompose to produce primary free radicals and activate free radical polymerization of wall-forming monomers at low temperature, hence could not only trigger the reaction effectively and completely, but also reduce the energy consumption greatly.

Another object of the present invention is to provide a method for preparing thermosensitive nanocapsules, wherein the reaction method is the miniemulsion polymerization, during which the reaction system nucleates into sub-micron droplets where polymer shell forms from the free radical polymerization of monomer in oil phase activated by initiator under a certain temperature and nitrogen atmosphere to fully cover the surface of core material, promising a high embedding rate.

Accordingly, to achieve above mentioned objects, the present invention provides a composition and a method of preparation including the following steps:

a) making emulsifier aqueous solution, i.e., mixing emulsifier and deionized water to form water phase;

b) mixing and fully stirring core material, two different N-alkyl acrylamide monomers, crosslinking agent, initiator and co-stabilizer to form oil phase;

c) adding water phase to oil phase, then, in succession, forming microemulsion by shearing and nanoemulsion via sonication;

d) introducing nitrogen into nanoemulsion and carrying out reaction under 40-80° C., finally obtaining thermosensitive nanocapsules;

herein said N-alkyl acrylamide possessing a general formula of $R_1$: —$C_{m_2}H_{2m_1+1}$;
$R_2$: —$C_{m_2}H_{2m_2+1}$, or —H;
$m_1$=2, 3, 4, . . . ;
$m_2$=1, 2, 3, 4, . . . ;
herein said crosslinking agent possessing a general formula of $n_1$=2, 3, 4 . . . ; $n_2$=1, 2, 3, 4 . . . ; $n_3$=2, 3, 4 . . . ; $n_4$=1, 2, 3, 4 . . . ;
$n_5$=2, 3, 4 . . . ; $n_6$=1, 2, 3, 4 . . . ; $n_7$=2, 3, 4 . . . ; $n_8$=1, 2, 3, 4 . . . .

DETAILED DESCRIPTION OF THE EMBODIMENTS

Figure 1:
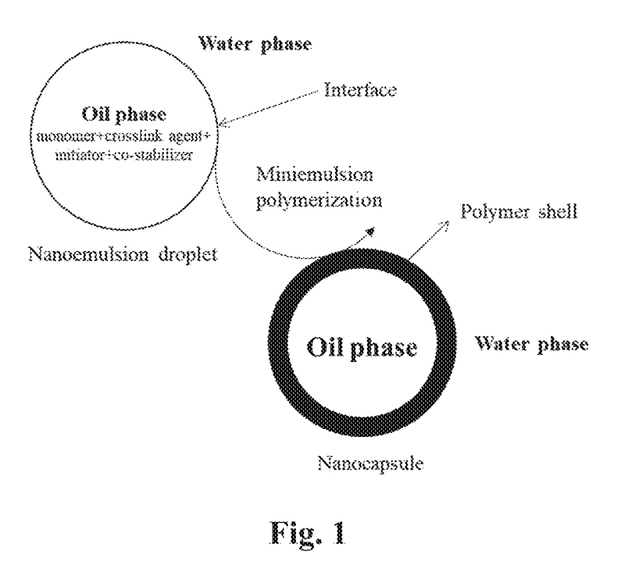
FIG. 1 is a sketch map showing the mechanism of polymer shell formation from the free radical polymerization of monomer in oil phase activated by initiator under a certain temperature and nitrogen atmosphere.

Referring to FIG. 1, a method for preparing thermosensitive nanocapsules according to the preferred embodiment of the present invention is illustrated; the method comprises the following steps:

a) making emulsifier aqueous solution, i.e., mixing emulsifier and deionized water to form water phase;

b) mixing and fully stirring core material, two different N-alkyl acrylamide monomers, crosslinking agent, initiator and co-stabilizer to form oil phase;

c) adding water phase to oil phase, then, in succession, forming microemulsion by shearing and nanoemulsion via sonication;

d) introducing nitrogen into nanoemulsion and carrying out reaction under 40-80° C., finally obtaining thermosensitive nanocapsules.

In step (a), the emulsifier is one of sodium dodecyl sulfonate, arabic gum or polyvinyl alcohol with a hydrolysis degree of 80-90%.

In step (b), the core material is at least one of ultraviolet absorber, flavor/fragrance, phase change material or pharmaceutical; furthermore, herein said ultraviolet absorbent is one of octocrylene, benzophenone-3, octyl salicylate, avobenzone or iso-octyl methoxycinnamate; said flavor/fragrance is one of peppermint oil, rose flavor, lemon flavor, lavender flavor, green tea flavor, lotus flavor or flower fragrance; said phase change material is one of paraffin, n-tetradecane, n-pentadecane, n-hexadecane, n-heptadecane, n-octadecane, n-nonadecane, n-eicosane, n-heneicosane, n-docosane, n-tricosane or n-tetracosane; said pharmaceutical is one of vitamin oil or antineoplastic drugs.

In step (b), the monomer is one of N,N-diethyl acrylamide, N,N-dimethyl acrylamide, N-isopropyl acrylamide, N-ethyl acrylamide, N-tert-butyl acrylamide, N-n-propyl acrylamide or N-methyl-N-ethyl acrylamide.

In step (b), the crosslinking agent is at least one of ethylene glycol dimethacrylate, 1,4-butanediol dimethacrylate or 1,6-hexanediol dimethacrylate.

In step (b), the initiator is one of azobisisobutyronitrile or benzoyl peroxide, and the co-stabilizer is one of hexadecane, hexadecanol or octadecyl mercaptan.

In step (c), the water phase and oil phase, counted by weight parts, possess the composition of

| | |
|---|---|
| emulsifier | 1.5-4.5phr; |
| deionized water | 10-90phr; |
| core material | 10-120phr; |
| one N-alkyl acrylamide | 6-14phr; |
| the other N-alkyl acrylamide | 6-14phr; |
| crosslinking agent | 1-5phr; |
| initiator | 0.1-0.8phr; |
| co-stabilizer | 1-2.5phr. |

In step (c), the shearing possesses a rate of 6000-10000 rpm, a time of 3-6 min, and the sonication possesses an amplitude of 50%, a time of 10-30 min.

In step (d), introducing nitrogen means maintaining the protection nitrogen atmosphere for the nanoemulsion system till the ending of reaction, and the reaction has a time of 3-4 hr.

In step (d), the obtained thermosensitive nanocapsules, in which core material is embedded in wall material formed through free radical polymerization in the water/oil interface of monomers from oil phase, possess a embedding rate of 90-94%, a particle size of less than 150 nm and a dimension polydispersity index of 0.09-0.17.

In conclusion, the present invention provides the composition and method for preparing thermosensitive nanocapsules, i.e., with the novel polymer shell formed from the free radical polymerization of two kinds of N-alkyl acrylamide monomer as wall material, and more than one material of ultraviolet absorbers, flavors and fragrances, phase change materials and medicines as core material, the nanocapsules being prepared via the miniemulsion polymerization. Specifically, the water phase is the aqueous solution of water-soluble emulsifier, whereas the oil phase is the mixture of core material, two different N-alkyl acrylamide monomers, crosslinking agent, initiator and co-stabilizer. Then, the mixture, in succession, forms microemulsion by shearing and nanoemulsion via sonication. Subsequently, polymer shell forms from the free radical polymerization of monomer in oil phase activated by initiator under a certain temperature and nitrogen atmosphere, to fully cover the surface of core material.

The mechanism of adopted miniemulsion polymerization is described as follows:

The miniemulsion polymerization is defined as a reaction process carried out in the sub-micron (50-500 nm) droplet nucleus stably dispersed in the so-called miniemulsion. In such miniemulsion system, due to the interaction of emulsifiers and stabilizers, a stable and uniform submicron monomer droplet is formed. Compared with the large monomer droplets of the traditional emulsion, the surface area of droplets in the miniemulsion is greatly increased, so that most of the emulsifiers are adsorbed on the surface of these droplets. As a result, there are not enough free emulsifiers in the water phase to form micelles or stable homogeneous nucleation, therefore, the droplets become the main place for reaction nucleation. Miniemulsion polymerization not only retains most of the advantages of traditional emulsion polymerization, but also has unique characteristics, extending the application scope of emulsion polymerization.

Moreover, the compounds used in the present invention, such as N, N-diethyl acrylamide and N, N-dimethyl acrylamide, can act as both monomer and crosslinking agent due to their unique structures just demonstrated as follows:

Based on above mentioned method, the following examples are carried out for further demonstration in the present invention.

EXAMPLE 1-5

A method for preparing thermosensitive nanocapsules, comprising the steps:

1. Dissolve 1.5 phr of sodium dodecyl sulfonate in 10 phr of deionized water to obtain water phase.
2. Mix 10 phr of core material, 6 phr of N,N-diethyl acrylamide, 6 phr of N,N-dimethyl acrylamide, 1 phr of ethylene glycol dimethacrylate, 0.1 phr of azobisisobutyronitrile and 1 phr of hexadecane uniformly to obtain oil phase.
3. Add water phase to oil phase, then form microemulsion by means of shearing with a rate of 6000 rpm for 3 min and furtherly form nanoemulsion via sonication with an amplitude of 50% for 10 min.
4. Introduce nitrogen into the nanoemulsion continually to protect the reaction carried out under 40° C. for 3 hr, then the thermosensitive nanocapsules are obtained.

When the core material is one of octocrylene, benzophenone-3, octyl salicylate, avobenzone or iso-octyl methoxycinnamate, respectively, the obtained thermosensitive nanocapsules are those embedding core material in the polymer shell formed from the free radical polymerization of monomer from oil phase in the water/oil interface. The basic characteristics of those thermosensitive nanocapsules are listed in the following table:

|  | Core material | Embedding rate (%) | Dimension PDI | Particle size(nm) |
| --- | --- | --- | --- | --- |
| Example 1 | octocrylene | 90 | 0.09 | 140-150 |
| Example 2 | benzophenone-3 | 91 | 0.1 | 130-150 |
| Example 3 | octyl salicylate | 90 | 0.09 | 110-140 |
| Example 4 | avobenzone | 93 | 0.15 | 120-140 |
| Example 5 | iso-octyl methoxycinnamate | 92 | 0.13 | 130-150 |

EXAMPLE 6-10

A method for preparing thermosensitive nanocapsules, comprising the steps:

1. Dissolve 2 phr of sodium dodecyl sulfonate in 15 phr of deionized water to obtain water phase.
2. Mix 20 phr of core material, 8 phr of N,N-diethyl acrylamide, 6 phr of N,N-dimethyl acrylamide, 5 phr of 1,4-butanediol dimethacrylate, 0.2 phr of azobisisobutyronitrile and 1.1 phr of hexadecane uniformly to obtain oil phase.
3. Add water phase to oil phase, then form microemulsion by means of shearing with a rate of 6500 rpm for 4 min and furtherly form nanoemulsion via sonication with an amplitude of 50% for 12 min.
4. Introduce nitrogen into the nanoemulsion continually to protect the reaction carried out under 42° C. for 4 hr, then the thermosensitive nanocapsules are obtained.

When the core material is one of peppermint oil, rose flavor, lemon flavor, lavender flavor or green tea flavor, respectively, the obtained thermosensitive nanocapsules are those embedding core material in the polymer shell formed from the free radical polymerization of monomer from oil phase in the water/oil interface. The basic characteristics of those thermosensitive nanocapsules are listed in the following table:

|  | Core material | Embedding rate (%) | Dimension PDI | Particle size(nm) |
| --- | --- | --- | --- | --- |
| Example 6 | peppermint oil | 91 | 0.12 | 140-150 |
| Example 7 | rose flavor | 92 | 0.13 | 130-150 |
| Example 8 | lemon flavor | 90 | 0.11 | 130-140 |
| Example 9 | lavender flavor | 93 | 0.14 | 120-130 |
| Example 10 | green tea flavor | 92 | 0.09 | 110-130 |

EXAMPLE 11-15

A method for preparing thermosensitive nanocapsules, comprising the steps:

1. Dissolve 3 phr of sodium dodecyl sulfonate in 20 phr of deionized water to obtain water phase.
2. Mix 50 phr of lotus flavor, N,N-diethyl acrylamide, N,N-dimethyl acrylamide, 2 phr of 1,6-hexanediol dimethacrylate, 0.3 phr of azobisisobutyronitrile and 1.2 phr of hexadecane uniformly to obtain oil phase.
3. Add water phase to oil phase, then form microemulsion by means of shearing with a rate of 7000 rpm for 5 min and furtherly form nanoemulsion via sonication with an amplitude of 50% for 15 min.
4. Introduce nitrogen into the nanoemulsion continually to protect the reaction carried out under 45° C. for 3 hr, then the thermosensitive nanocapsules are obtained.

When the weight fraction of N,N-diethyl acrylamide is 14 phr, 12 phr, 10 phr, 8 phr or 6 phr, whereas the weight fraction of N,N-dimethyl acrylamide is 6 phr, 8 phr, 10 phr, 12 phr or 14 phr, respectively, the obtained thermosensitive nanocapsules are those embedding lotus flavor in the polymer shell formed from the free radical polymerization of monomer from oil phase in the water/oil interface. The basic characteristics of those thermosensitive nanocapsules are listed in the following table:

|  | N,N-diethyl acrylamide (phr) | N,N-dimethyl acrylamide (phr) | Phase change temperature (° C.) | Embedding rate (%) | Dimension PDI | Particle size (nm) |
|---|---|---|---|---|---|---|
| Example 11 | 14 | 6 | 46 | 91 | 0.12 | 140-150 |
| Example 12 | 12 | 8 | 54 | 92 | 0.13 | 130-150 |
| Example 13 | 10 | 10 | 61 | 90 | 0.11 | 130-140 |
| Example 14 | 8 | 12 | 67 | 93 | 0.14 | 120-130 |
| Example 15 | 6 | 14 | 69 | 92 | 0.09 | 110-130 |

EXAMPLE 16

A method for preparing thermosensitive nanocapsules, comprising the steps:

1. Dissolve 4.5 phr of arabic gum in 26 phr of deionized water to obtain water phase.

2. Mix 66 phr of flower fragrance, 7 phr of N-isopropyl acrylamide, 8 phr of N-ethyl acrylamide, 3 phr of mixture of ethylene glycol dimethacrylate and 1,4-butanediol dimethacrylate (weight ratio 1:1), 0.4 phr of azobisisobutyronitrile and 1.5 phr of hexadecane uniformly to obtain oil phase.

3. Add water phase to oil phase, then form microemulsion by means of shearing with a rate of 7500 rpm for 6 min and furtherly form nanoemulsion via sonication with an amplitude of 50% for 18 min.

4. Introduce nitrogen into the nanoemulsion continually to protect the reaction carried out under 46° C. for 3 hr, then the thermosensitive nanocapsules are obtained. During the reaction, the dispersed oil phase nucleates sub-micron droplets, in which azobisisobutyronitrile initiate the free radical polymerization between N-isopropyl acrylamide and N-ethyl acrylamide to form polymer shell, just illustrated in FIG. 1.

Figure 2:
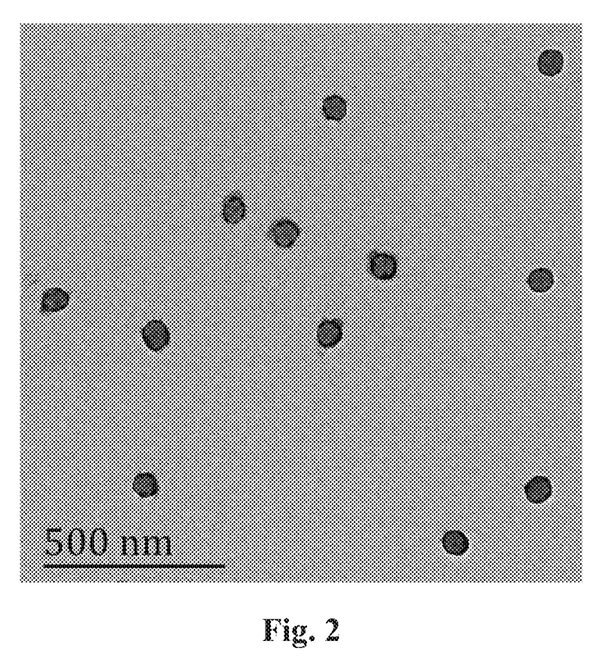
FIG. 2 is schematic view of transmission electron microscope (TEM) of nanocapsules.
Figure 3:
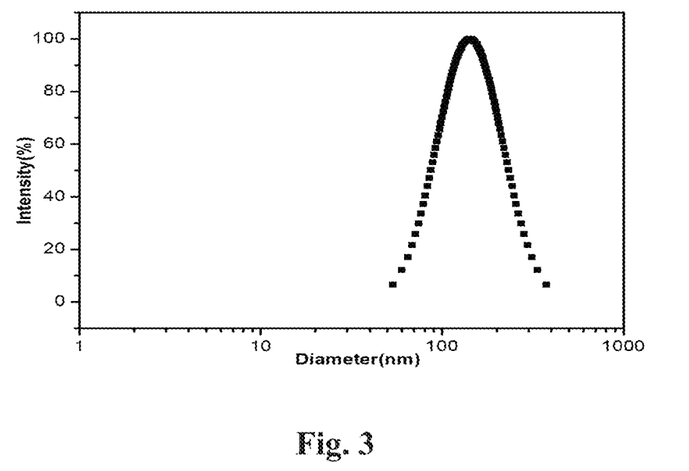
FIG. 3 is schematic view illustrating the size distribution of nanocapsules.
Figure 4:
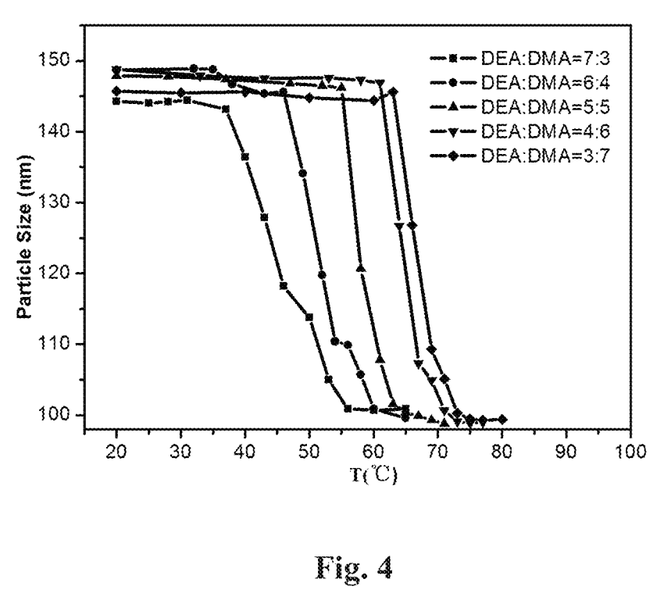
FIG. 4 is schematic view illustrating the thermosensitivity of nanocapsules.

The testing results show that the obtained thermosensitive nanocapsules are those embedding flower fragrance in the polymer shell formed from the free radical polymerization of monomer from oil phase in the water/oil interface, especially, under TEM it has been found that the nanocapsules have a sphere shape and a core-shell structure with good dispersion without obvious aggregation, just illustrated in FIG. 2. Moreover, the obtained nanocapsules possess a embedding rate of 93%, a particle size of 140-149 nm and a dimension polydispersity index of 0.1, just illustrated in FIG. 3.

EXAMPLE 17

A method for preparing thermosensitive nanocapsules, comprising the steps:

1. Dissolve 4 phr of arabic gum in 30 phr of deionized water to obtain water phase.

2. Mix 70 phr of paraffin, 9 phr of N-isopropyl acrylamide, 10 phr of N-ethyl acrylamide, 4 phr of mixture of 1,4-butanediol dimethacrylate and 1,6-hexanediol dimethacrylate (weight ratio 1:2), 0.5 phr of azobisisobutyronitrile and 1.6 phr of hexadecane uniformly to obtain oil phase.

3. Add water phase to oil phase, then form microemulsion by means of shearing with a rate of 8000 rpm for 3 min and furtherly form nanoemulsion via sonication with an amplitude of 50% for 20 min.

4. Introduce nitrogen into the nanoemulsion continually to protect the reaction carried out under 50° C. for 3 hr, then the thermosensitive nanocapsules are obtained.

The testing results show that the obtained thermosensitive nanocapsules are those embedding paraffin in the polymer shell formed from the free radical polymerization of monomer from oil phase in the water/oil interface, possessing a embedding rate of 94%, a particle size of 110-130 nm and a dimension polydispersity index of 0.15.

EXAMPLE 18

A method for preparing thermosensitive nanocapsules, comprising the steps:

1. Dissolve 3 phr of arabic gum in 35 phr of deionized water to obtain water phase.

2. Mix 75 phr of n-tetradecane, 11 phr of N-isopropyl acrylamide, 12 phr of N-ethyl acrylamide, 5 phr of mixture of ethylene glycol dimethacrylate, 1,4-butanediol dimethacrylate and 1,6-hexanediol dimethacrylate (weight ratio 1:1:1), 0.6 phr of azobisisobutyronitrile and 1.7 phr of hexadecane uniformly to obtain oil phase.

3. Add water phase to oil phase, then form microemulsion by means of shearing with a rate of 8500 rpm for 3 min and furtherly form nanoemulsion via sonication with an amplitude of 50% for 22 min.

4. Introduce nitrogen into the nanoemulsion continually to protect the reaction carried out under 52° C. for 4 hr, then the thermosensitive nanocapsules are obtained.

The testing results show that the obtained thermosensitive nanocapsules are those embedding n-tetradecane in the polymer shell formed from the free radical polymerization of monomer from oil phase in the water/oil interface, possessing a embedding rate of 94%, a particle size of 130-149 nm and a dimension polydispersity index of 0.15.

EXAMPLE 19

A method for preparing thermosensitive nanocapsules, comprising the steps:

1. Dissolve 1.5 phr of polyvinyl alcohol with a hydrolysis degree of 80% in 40 phr of deionized water to obtain water phase.

2. Mix 80 phr of n-pentadecane, 13 phr of N-tert-butyl acrylamide, 14 phr of N-n-propyl acrylamide, 1 phr of ethylene glycol dimethacrylate, 0.7 phr of azobisisobutyronitrile and 1.8 phr of hexadecanol uniformly to obtain oil phase.

3. Add water phase to oil phase, then form microemulsion by means of shearing with a rate of 9000 rpm for 3 min and furthely form nanoemulsion via sonication with an amplitude of 50% for 23 min.

4. Introduce nitrogen into the nanoemulsion continually to protect the reaction carried out under 55° C. for 4 hr, then the thermosensitive nanocapsules are obtained.

The testing results show that the obtained thermosensitive nanocapsules are those embedding n-pentadecane in the polymer shell formed from the free radical polymerization of monomer from oil phase in the water/oil interface, possessing a embedding rate of 91%, a particle size of 110-130 nm and a dimension polydispersity index of 0.11.

EXAMPLE 20

A method for preparing thermosensitive nanocapsules, comprising the steps:

1. Dissolve 2 phr of polyvinyl alcohol with a hydrolysis degree of 80% in 45 phr of deionized water to obtain water phase.

2. Mix 85 phr of n-hexadecane, 12 phr of N-tert-butyl acrylamide, 14 phr of N-n-propyl acrylamide, 2 phr of ethylene glycol dimethacrylate, 0.8 phr of benzoyl peroxide and 1.9 phr of hexadecanol uniformly to obtain oil phase.

3. Add water phase to oil phase, then form microemulsion by means of shearing with a rate of 9500 rpm for 3 min and furthely form nanoemulsion via sonication with an amplitude of 50% for 24 min.

4. Introduce nitrogen into the nanoemulsion continually to protect the reaction carried out under 60° C. for 3 hr, then the thermosensitive nanocapsules are obtained.

The testing results show that the obtained thermosensitive nanocapsules are those embedding n-hexadecane in the polymer shell formed from the free radical polymerization of monomer from oil phase in the water/oil interface, possessing a embedding rate of 92%, a particle size of 110-130 nm and a dimension polydispersity index of 0.11.

EXAMPLE 21

A method for preparing thermosensitive nanocapsules, comprising the steps:

1. Dissolve 3 phr of polyvinyl alcohol with a hydrolysis degree of 80% in 50 phr of deionized water to obtain water phase.

2. Mix 90 phr of n-heptadecane, 8 phr of N-tert-butyl acrylamide, 13 phr of N-n-propyl acrylamide, 3 phr of ethylene glycol dimethacrylate, 0.1 phr of benzoyl peroxide and 2 phr of hexadecanol uniformly to obtain oil phase.

3. Add water phase to oil phase, then form microemulsion by means of shearing with a rate of 10000 rpm for 4 min and furthely form nanoemulsion via sonication with an amplitude of 50% for 25 min.

4. Introduce nitrogen into the nanoemulsion continually to protect the reaction carried out under 62° C. for 3 hr, then the thermosensitive nanocapsules are obtained.

The testing results show that the obtained thermosensitive nanocapsules are those embedding n-heptadecane in the polymer shell formed from the free radical polymerization of monomer from oil phase in the water/oil interface, possessing a embedding rate of 93%, a particle size of 110-130 nm and a dimension polydispersity index of 0.12.

EXAMPLE 22

A method for preparing thermosensitive nanocapsules, comprising the steps:

1. Dissolve 1.5 phr of polyvinyl alcohol with a hydrolysis degree of 85% in 55 phr of deionized water to obtain water phase.

2. Mix 95 phr of n-octadecane, 7 phr of N-methyl-N-ethyl acrylamide, 6 phr of N,N-diethyl acrylamide, 4 phr of ethylene glycol dimethacrylate, 0.2 phr of benzoyl peroxide and 2.1 phr of hexadecanol uniformly to obtain oil phase.

3. Add water phase to oil phase, then form microemulsion by means of shearing with a rate of 6000 rpm for 4 min and furthely form nanoemulsion via sonication with an amplitude of 50% for 26 min.

4. Introduce nitrogen into the nanoemulsion continually to protect the reaction carried out under 65° C. for 4 hr, then the thermosensitive nanocapsules are obtained.

The testing results show that the obtained thermosensitive nanocapsules are those embedding n-octadecane in the polymer shell formed from the free radical polymerization of monomer from oil phase in the water/oil interface, possessing a embedding rate of 94%, a particle size of 110-130 nm and a dimension polydispersity index of 0.12.

EXAMPLE 23

A method for preparing thermosensitive nanocapsules, comprising the steps:

1. Dissolve 3 phr of polyvinyl alcohol with a hydrolysis degree of 85% in 60 phr of deionized water to obtain water phase.

2. Mix 100 phr of n-nonadecane, 9 phr of N-methyl-N-ethyl acrylamide, 8 phr of N,N-diethyl acrylamide, 5 phr of 1,4-butanediol dimethacrylate, 0.3 phr of benzoyl peroxide and 2.2 phr of hexadecanol uniformly to obtain oil phase.

3. Add water phase to oil phase, then form microemulsion by means of shearing with a rate of 6200 rpm for 4 min and furthely form nanoemulsion via sonication with an amplitude of 50% for 28 min.

4. Introduce nitrogen into the nanoemulsion continually to protect the reaction carried out under 66° C. for 4 hr, then the thermosensitive nanocapsules are obtained.

The testing results show that the obtained thermosensitive nanocapsules are those embedding n-nonadecane in the polymer shell formed from the free radical polymerization of monomer from oil phase in the water/oil interface, possessing a embedding rate of 90%, a particle size of 110-130 nm and a dimension polydispersity index of 0.13.

EXAMPLE 24

A method for preparing thermosensitive nanocapsules, comprising the steps:

1. Dissolve 4.5 phr of polyvinyl alcohol with a hydrolysis degree of 85% in 65 phr of deionized water to obtain water phase.

2. Mix 105 phr of n-eicosane, 11 phr of N-methyl-N-ethyl acrylamide, 10 phr of N,N-diethyl acrylamide, 1 phr of 1,4-butanediol dimethacrylate, 0.4 phr of benzoyl peroxide and 2.3 phr of hexadecanol uniformly to obtain oil phase.

3. Add water phase to oil phase, then form microemulsion by means of shearing with a rate of 6600 rpm for 5 min and furthely form nanoemulsion via sonication with an amplitude of 50% for 29 min.

4. Introduce nitrogen into the nanoemulsion continually to protect the reaction carried out under 68° C. for 4 hr, then the thermosensitive nanocapsules are obtained.

The testing results show that the obtained thermosensitive nanocapsules are those embedding n-eicosane in the polymer shell formed from the free radical polymerization of monomer from oil phase in the water/oil interface, possessing a embedding rate of 90%/a, a particle size of 110-130 nm and a dimension polydispersity index of 0.13.

EXAMPLE 25

A method for preparing thermosensitive nanocapsules, comprising the steps:

1. Dissolve 1.8 phr of polyvinyl alcohol with a hydrolysis degree of 86% in 70 phr of deionized water to obtain water phase.

2. Mix 110 phr of n-heneicosane, 11 phr of N,N-dimethyl acrylamide, 8 phr of N-methyl-N-ethyl acrylamide, 2 phr of 1,4-butanediol dimethacrylate, 0.5 phr of benzoyl peroxide and 2.4 phr of hexadecanol uniformly to obtain oil phase.

3. Add water phase to oil phase, then form microemulsion by means of shearing with a rate of 6800 rpm for 5 min and furthery form nanoemulsion via sonication with an amplitude of 50% for 30 min.

4. Introduce nitrogen into the nanoemulsion continually to protect the reaction carried out under 70° C. for 3 hr, then the thermosensitive nanocapsules are obtained.

The testing results show that the obtained thermosensitive nanocapsules are those embedding n-heneicosane in the polymer shell formed from the free radical polymerization of monomer from oil phase in the water/oil interface, possessing a embedding rate of 91%, a particle size of 110-130 nm and a dimension polydispersity index of 0.14.

EXAMPLE 26

A method for preparing thermosensitive nanocapsules, comprising the steps:

1. Dissolve 2.2 phr of polyvinyl alcohol with a hydrolysis degree of 86% in 75 phr of deionized water to obtain water phase.

2. Mix 115 phr of n-docosane, 13 phr of N,N-dimethyl acrylamide, 10 phr of N-methyl-N-ethyl acrylamide, 3 phr of 1,4-butanediol dimethacrylate, 0.6 phr of benzoyl peroxide and 2.5 phr of hexadecanol uniformly to obtain oil phase.

3. Add water phase to oil phase, then form microemulsion by means of shearing with a rate of 7000 rpm for 5 min and furthery form nanoemulsion via sonication with an amplitude of 50% for 10 min.

4. Introduce nitrogen into the nanoemulsion continually to protect the reaction carried out under 72° C. for 3 hr, then the thermosensitive nanocapsules are obtained.

The testing results show that the obtained thermosensitive nanocapsules are those embedding n-docosane in the polymer shell formed from the free radical polymerization of monomer from oil phase in the water/oil interface, possessing a embedding rate of 91%, a particle size of 90-110 nm and a dimension polydispersity index of 0.14.

EXAMPLE 27

A method for preparing thermosensitive nanocapsules, comprising the steps:

1. Dissolve 2.8 phr of polyvinyl alcohol with a hydrolysis degree of 86% in 80 phr of deionized water to obtain water phase.

2. Mix 120 phr of n-tricosane, 14 phr of N,N-dimethyl acrylamide, 12 phr of N-methyl-N-ethyl acrylamide, 4 phr of 1,4-butanediol dimethacrylate, 0.1 phr of azobisisobutyronitrile and 1 phr of octadecyl mercaptan uniformly to obtain oil phase.

3. Add water phase to oil phase, then form microemulsion by means of shearing with a rate of 7500 rpm for 6 min and furthery form nanoemulsion via sonication with an amplitude of 50% for 11 min.

4. Introduce nitrogen into the nanoemulsion continually to protect the reaction carried out under 75° C. for 4 hr, then the thermosensitive nanocapsules are obtained.

The testing results show that the obtained thermosensitive nanocapsules are those embedding n-tricosane in the polymer shell formed from the free radical polymerization of monomer from oil phase in the water/oil interface, possessing a embedding rate of 92%, a particle size of 90-110 nm and a dimension polydispersity index of 0.15.

EXAMPLE 28

A method for preparing thermosensitive nanocapsules, comprising the steps:

1. Dissolve 1.5 phr of polyvinyl alcohol with a hydrolysis degree of 88% in 85 phr of deionized water to obtain water phase.

2. Mix 100 phr of n-tetracosane, 6 phr of N-isopropyl acrylamide, 7 phr of N-tert-butyl acrylamide, 3 phr of 1,6-hexanediol dimethacrylate, 0.2 phr of azobisisobutyronitrile and 1.5 phr of octadecyl mercaptan uniformly to obtain oil phase.

3. Add water phase to oil phase, then form microemulsion by means of shearing with a rate of 8000 rpm for 6 min and furthery form nanoemulsion via sonication with an amplitude of 50% for 12 min.

4. Introduce nitrogen into the nanoemulsion continually to protect the reaction carried out under 76° C. for 4 hr, then the thermosensitive nanocapsules are obtained.

The testing results show that the obtained thermosensitive nanocapsules are those embedding n-tetracosane in the polymer shell formed from the free radical polymerization of monomer from oil phase in the water/oil interface, possessing a embedding rate of 92%, a particle size of 90-110 nm and a dimension polydispersity index of 0.15.

EXAMPLE 29

A method for preparing thermosensitive nanocapsules, comprising the steps:

1. Dissolve 2 phr of polyvinyl alcohol with a hydrolysis degree of 88% in 90 phr of deionized water to obtain water phase.

2. Mix 130 phr of vitamin oil, 9 phr of N-isopropyl acrylamide, 10 phr of N-tert-butyl acrylamide, 4 phr of 1,6-hexanediol dimethacrylate, 0.3 phr of azobisisobutyronitrile and 1.6 phr of octadecyl mercaptan uniformly to obtain oil phase.

3. Add water phase to oil phase, then form microemulsion by means of shearing with a rate of 8200 rpm for 6 min and furthery form nanoemulsion via sonication with an amplitude of 50% for 15 min.

4. Introduce nitrogen into the nanoemulsion continually to protect the reaction carried out under 78° C. for 3 hr, then the thermosensitive nanocapsules are obtained.

The testing results show that the obtained thermosensitive nanocapsules are those embedding vitamin oil in the polymer shell formed from the free radical polymerization of monomer from oil phase in the water/oil interface, possessing a embedding rate of 93%, a particle size of 90-110 nm and a dimension polydispersity index of 0.15.

EXAMPLE 30

A method for preparing thermosensitive nanocapsules, comprising the steps:
1. Dissolve 3 phr of polyvinyl alcohol with a hydrolysis degree of 88% in 10 phr of deionized water to obtain water phase.
2. Mix 110 phr of antineoplastic drugs, 12 phr of N-isopropyl acrylamide, 14 phr of N-tert-butyl acrylamide, 5 phr of 1,6-hexanediol dimethacrylate, 0.4 phr of benzoyl peroxide and 1.8 phr of octadecyl mercaptan uniformly to obtain oil phase.
3. Add water phase to oil phase, then form microemulsion by means of shearing with a rate of 9000 rpm for 3 min and furtherly form nanoemulsion via sonication with an amplitude of 50% for 16 min.
4. Introduce nitrogen into the nanoemulsion continually to protect the reaction carried out under 60° C. for 4 hr, then the thermosensitive nanocapsules are obtained.
The testing results show that the obtained thermosensitive nanocapsules are those embedding antineoplastic drugs in the polymer shell formed from the free radical polymerization of monomer from oil phase in the water/oil interface, possessing a embedding rate of 93%, a particle size of 90-110 nm and a dimension polydispersity index of 0.16.

EXAMPLE 31

A method for preparing thermosensitive nanocapsules, comprising the steps:
1. Dissolve 1.5 phr of polyvinyl alcohol with a hydrolysis degree of 90% in 35 phr of deionized water to obtain water phase.
2. Mix 116 phr of mixture of octocrylene and rose flavor (weight ratio 1:1), 6 phr of N-ethyl acrylamide, 10 phr of N-n-propyl acrylamide, 2 phr of mixture of ethylene glycol dimethacrylate and 1,4-butanediol dimethacrylate (weight ratio 1:1), 0.5 phr of azobisisobutyronitrile and 2 phr of octadecyl mercaptan uniformly to obtain oil phase.
3. Add water phase to oil phase, then form microemulsion by means of shearing with a rate of 9200 rpm for 4 min and furtherly form nanoemulsion via sonication with an amplitude of 50% for 18 min.
4. Introduce nitrogen into the nanoemulsion continually to protect the reaction carried out under 66° C. for 3 hr, then the thermosensitive nanocapsules are obtained.
The testing results show that the obtained thermosensitive nanocapsules are those embedding core materials in the polymer shell formed from the free radical polymerization of monomer from oil phase in the water/oil interface, possessing a embedding rate of 94%, a particle size of 90-110 nm and a dimension polydispersity index of 0.16.

EXAMPLE 32

A method for preparing thermosensitive nanocapsules, comprising the steps:
1. Dissolve 2 phr of polyvinyl alcohol with a hydrolysis degree of 90% in 52 phr of deionized water to obtain water phase.
2. Mix 118 phr of mixture of benzophenone-3, rose flavor, paraffin and antineoplastic drugs (weight ratio 1:1:1:1), 12 phr of N-ethyl acrylamide, 12 phr of N-n-propyl acrylamide, 3 phr of mixture of 1,4-butanediol dimethacrylate and 1,6-hexanediol dimethacrylate (weight ratio 1:2), 0.6 phr of azobisisobutyronitrile and 2.2 phr of octadecyl mercaptan uniformly to obtain oil phase.
3. Add water phase to oil phase, then form microemulsion by means of shearing with a rate of 9500 rpm for 5 min and furtherly form nanoemulsion via sonication with an amplitude of 50% for 20 min.
4. Introduce nitrogen into the nanoemulsion continually to protect the reaction carried out under 75° C. for 4 hr, then the thermosensitive nanocapsules are obtained.
The testing results show that the obtained thermosensitive nanocapsules are those embedding core materials in the polymer shell formed from the free radical polymerization of monomer from oil phase in the water/oil interface, possessing a embedding rate of 94%, a particle size of 90-110 nm and a dimension polydispersity index of 0.17.

EXAMPLE 33

A method for preparing thermosensitive nanocapsules, comprising the steps:
1. Dissolve 3 phr of polyvinyl alcohol with a hydrolysis degree of 90% in 63 phr of deionized water to obtain water phase.
2. Mix 150 phr of mixture of avobenzone, flower fragrance and n-heptadecane (weight ratio 1:1:1), 14 phr of N-ethyl acrylamide, 14 phr of N-n-propyl acrylamide, 4 phr of mixture of ethylene glycol dimethacrylate, 1,4-butanediol dimethacrylate and 1,6-hexanediol dimethacrylate (weight ratio 1:1:1), 0.8 phr of benzoyl peroxide and 2.5 phr of octadecyl mercaptan uniformly to obtain oil phase.
3. Add water phase to oil phase, then form microemulsion by means of shearing with a rate of 10000 rpm for 6 min and furtherly form nanoemulsion via sonication with an amplitude of 50% for 30 min.
4. Introduce nitrogen into the nanoemulsion continually to protect the reaction carried out under 80° C. for 3 hr, then the thermosensitive nanocapsules are obtained.
The testing results show that the obtained thermosensitive nanocapsules are those embedding core materials in the polymer shell formed from the free radical polymerization of monomer from oil phase in the water/oil interface, possessing a embedding rate of 94%, a particle size of 90-110 nm and a dimension polydispersity index of 0.17.

What is claimed is:
1. A method for preparing thermosensitive nanocapsules, wherein the thermosensitive nanocapsules are prepared by forming a wall material from a free radical polymerization of two different N-alkyl acrylamide monomers; the method comprises the following steps:
(1) making an emulsifier aqueous solution by mixing an emulsifier and deionized water to form a water phase;
(2) mixing and fully stirring a core material, the two different N-alkyl acrylamide monomers, a crosslinking agent, an initiator and a co-stabilizer to form an oil phase;
(3) adding the water phase to the oil phase, forming microemulsion by shearing, and then forming a nanoemulsion via sonication; and
(4) introducing nitrogen into the nanoemulsion and carrying out a reaction at 40-80° C., finally obtaining the thermosensitive nanocapsules;
wherein the two N-alkyl acrylamide have a general formula of wherein, $R_1$ is $-C_{m_1}H_{2m_1+1}$;
$R_2$ is $-C_{2_2}H_{2m_2+1}$, or $-H$;
$m_1 = 2, 3, 4, \ldots$;
$m_2 = 1, 2, 3, 4, \ldots$;
wherein, the crosslinking agent has a general formula of , or $-H$;

, or $-H$;

, or $-H$;

$n_1 = 2, 3, 4 \ldots$; $n_2 = 1, 2, 3, 4 \ldots$; $n_3 = 2, 3, 4 \ldots$; $n_4 = 1, 2, 3, 4 \ldots$;
$n_5 = 2, 3, 4 \ldots$; $n_6 = 1, 2, 3, 4 \ldots$; $n_7 = 2, 3, 4 \ldots$; $n_8 = 1, 2, 3, 4 \ldots$, wherein the core material is one or more selected from the group consisting of an ultraviolet absorber, a flavor or a fragrance, a phase change material and a pharmaceutical, wherein the ultraviolet absorbent is selected from the group consisting of octocrylene, benzophenone-3, octyl salicylate, avobenzone and iso-octyl methoxycinnamate; the flavor or the fragrance is selected from the group consisting of peppermint oil, rose flavor, lemon flavor, lavender flavor, green tea flavor, lotus flavor and flower fragrance; the phase change material is selected from the group consisting of paraffin, n-tetradecane, n-pentadecane, n-hexadecane, n-heptadecane, n-octadecane, n-nonadecane, n-eicosane, n-heneicosane, n-docosane, n-tricosane and n-tetracosane; and the pharmaceutical is selected from the group consisting of vitamin oil and antineoplastic drugs.

2. The method of claim 1, wherein the emulsifier is selected from the group consisting of sodium dodecyl sulfonate, arabic gum and polyvinyl alcohol with a hydrolysis degree of 80-90%.

3. The method of claim 1, wherein the two different N-alkyl acrylamide monomers are selected from the group consisting of N,N-diethyl acrylamide, N,N-dimethyl acrylamide, N-isopropyl acrylamide, N-ethyl acrylamide, N-tert-butyl acrylamide, N-n-propyl acrylamide and N-m ethyl -N-ethyl acrylamide.

4. The method of claim 1, wherein the crosslinking agent is one or more selected from the group consisting of ethylene glycol dimethacrylate, 1,4-butanediol dimethacrylate and 1,6-hexanediol dimethacrylate.

5. The method of claim 1, wherein the initiator is selected from the group consisting of azobisisobutyronitrile and benzoyl peroxide; and the co-stabilizer is selected from the group consisting of hexadecane, hexadecanol and octadecyl mercaptan.

6. The method of claim 1, wherein the water phase and the oil phase forming the microemulsion, wherein the microemulsion, by weight parts, has a composition of
   1.5-4.5 phr of the emulsifier;
   10-90 phr of the deionized water;
   10-120 phr of the core material;
   6-14 phr of a first acrylamide from the two N-alkyl acrylamide;
   6-14 phr of a second acrylamide from the two N-alkyl acrylamide;
   1-5 phr of the crosslinking agent;
   0.1-0.8 phr of the initiator; and
   1-2.5 phr of the co-stabilizer.

7. A method for preparing thermosensitive nanocapsules, wherein the thermosensitive nanocapsules are prepared by forming a wall material from a free radical polymerization of two different N-alkyl acrylamide monomers; the method comprises the following steps:
   (1) making an emulsifier aqueous solution by mixing an emulsifier and deionized water to form a water phase;
   (2) mixing and fully stirring a core material, the two different N-alkyl acrylamide monomers, a crosslinking agent, an initiator and a co-stabilizer to form an oil phase;
   (3) adding the water phase to the oil phase, forming microemulsion by shearing, and then forming a nanoemulsion via sonication; and
   (4) introducing nitrogen into the nanoemulsion and carrying out a reaction at 40-80° C., finally obtaining the thermosensitive nanocapsules;
   wherein the two N-alkyl acrylamide have a general formula of wherein, $R_1$ is $-C_{m_1}H_{2m_1+1}$;
$R_2$ is $-C_{m_2}H_{2m_2+1}$, or $-H$;
$m_1 = 2, 3, 4, \ldots$;
$m_2 = 1, 2, 3, 4, \ldots$;
wherein, the crosslinking agent has a general formula of $n_1=2, 3, 4 \ldots; n_2=1, 2, 3, 4 \ldots; n_3=2, 3, 4 \ldots; n_4=1, 2, 3, 4 \ldots;$
$n_5=2, 3, 4 \ldots; n_6=1, 2, 3, 4 \ldots; n_7=2, 3, 4 \ldots; n_8=1, 2, 3, 4 \ldots;$ wherein the shearing has a rate of 6000-10000 rpm and a time of 3-6 min, and the sonication has an amplitude of 50% and a time of 10-30 min.

8. The method of claim 1, wherein in the step (4), the protection nitrogen atmosphere for the nanoemulsion system is maintained till the ending of the reaction, and the reaction has a time of 3-4 hr.

9. A thermosensitive nanocapsule, prepared by the method of claim 1, comprising the core material and the wall material, wherein
the core material embedded in the wall material; the wall material is formed through the free radical polymerization in a water and oil interface of the two N-alkyl acrylamide monomers from the oil phase; the thermosensitive nanocapsule has an embedding rate of 90-94%, a particle size of less than 150 nm and a dimension polydispersity index of 0.09-0.17,
wherein the core material is one or more selected from the group consisting of an ultraviolet absorber, a flavor or a fragrance, a phase change material and a pharmaceutical, wherein the ultraviolet absorbent is selected from the group consisting of octocrylene, benzophenone-3, octyl salicylate, avobenzone and iso-octyl methoxycinnamate; the flavor or fragrance is selected from the group consisting of peppermint oil, rose flavor, lemon flavor, lavender flavor, green tea flavor, lotus flavor and flower fragrance; the phase change material is selected from the group consisting of paraffin, n-tetradecane, n-pentadecane, n-hexadecane, n-heptadecane, n-octadecane, n-nonadecane, n-eicosane, n-heneicosane, n-docosane, n-tricosane and n-tetracosane; and the pharmaceutical is selected from the group consisting of vitamin oil and antineoplastic drugs.

10. The thermosensitive nanocapsule of claim 9, wherein the emulsifier is selected from the group consisting of sodium dodecyl sulfonate, arabic gum and polyvinyl alcohol with a hydrolysis degree of 80-90%.

11. The thermosensitive nanocapsule of claim 9, wherein the two different N-alkyl acrylamide monomers are selected from the group consisting of N,N-diethyl acrylamide, N,N-dimethyl acrylamide, N-isopropyl acrylamide, N-ethyl acrylamide, N-tert-butyl acrylamide, N-n-propyl acrylamide and N-methyl-N-ethyl acrylamide.

12. The thermosensitive nanocapsule of claim 9, wherein the crosslinking agent is one or more selected from the group consisting of ethylene glycol dimethacrylate, 1,4-butanediol dimethacrylate and 1,6-hexanediol dimethacrylate.

13. The thermosensitive nanocapsule of claim 9, wherein the initiator is selected from the group consisting of azobisisobutyronitrile and benzoyl peroxide; and the co-stabilizer is one selected from the group consisting of hexadecane, hexadecanol and octadecyl mercaptan.

14. The thermosensitive nanocapsule of claim 9, wherein the water phase and the oil phase forming the microemulsion, wherein the microemulsion, by weight parts, has a composition of
1.5-4.5 phr of the emulsifier;
10-90 phr of the deionized water;
10-120 phr of the core material;
6-14 phr of a first acrylamide of the two N-alkyl acrylamide;
6-14 phr of a second acrylamide of the two N-alkyl acrylamide;
1-5 phr of the crosslinking agent;
0.1-0.8 phr of the initiator; and
1-2.5 phr of the co-stabilizer.

15. The thermosensitive nanocapsule of claim 9, wherein the shearing has a rate of 6000-10000 rpm and a time of 3-6 min, and the sonication has an amplitude of 50% and a time of 10-30 min.

16. The thermosensitive nanocapsule of claim 9, wherein in the step (4), the protection nitrogen atmosphere for the nanoemulsion system is maintained till the ending of the reaction, and the reaction has a time of 3-4 hr.

* * * * *